US006184413B1

(12) United States Patent
Davis et al.

(10) Patent No.: US 6,184,413 B1
(45) Date of Patent: Feb. 6, 2001

(54) SUPPORTED PHASE CATALYST

(75) Inventors: Mark E. Davis, Pasadena, CA (US); Kam To Wan, St. Louis, MO (US)

(73) Assignee: California Institute of Technology, Pasadena, CA (US)

( * ) Notice: Under 35 U.S.C. 154(b), the term of this patent shall be extended for 0 days.

(21) Appl. No.: 09/330,576

(22) Filed: Jun. 11, 1999

Related U.S. Application Data

(60) Division of application No. 08/838,730, filed on Apr. 10, 1997, now Pat. No. 5,935,892, which is a continuation-in-part of application No. 08/371,880, filed on Jan. 12, 1995, now Pat. No. 5,736,480, which is a continuation-in-part of application No. 08/199,086, filed on Feb. 22, 1994, now abandoned.

(51) Int. Cl.⁷ .................................................. C07C 69/66
(52) U.S. Cl. ........................................... 560/179; 562/490
(58) Field of Search ............................ 560/179; 562/490

(56) References Cited

U.S. PATENT DOCUMENTS

| | | | |
|---|---|---|---|
| 4,399,312 | 8/1983 | Russell et al. | 568/454 |
| 4,605,750 | 8/1986 | Kumobayashi et al. | 556/7 |
| 4,654,176 | 3/1987 | Dang et al. | 260/505 |
| 4,691,037 | 9/1987 | Yoshikawa et al. | 556/18 |
| 4,766,227 | 8/1988 | Sauo et al. | 556/21 |
| 4,947,003 | 8/1990 | Davis et al. | 568/454 |
| 4,954,644 | 9/1990 | Sayo et al. | 556/14 |
| 4,994,427 | 2/1991 | Davis et al. | 502/166 |
| 4,994,590 | 2/1991 | Takaya et al. | 556/21 |
| 5,012,002 | 4/1991 | Kumobayashi et al. | 568/17 |
| 5,159,093 | 10/1992 | Taketomi et al. | 556/136 |
| 5,177,231 | 1/1993 | Manimaran et al. | 556/21 |
| 5,187,135 | 2/1993 | Kolich et al. | 502/162 |
| 5,187,136 | 2/1993 | Klobucar et al. | 556/45 |
| 5,187,281 * | 2/1993 | Kolich et al. | 562/496 |
| 5,190,905 * | 3/1993 | Kolich et al. | 562/496 |
| 5,202,472 * | 4/1993 | Manimaman et al. | 562/493 |
| 5,202,473 * | 4/1993 | Chan et al. | 562/496 |
| 5,202,474 * | 4/1993 | Chan et al. | 562/496 |
| 5,210,243 | 5/1993 | Kolich | 556/18 |
| 5,223,648 | 6/1993 | Herrmann et al. | 568/429 |
| 5,274,146 | 12/1993 | Ishizaki et al. | 556/14 |
| 5,274,183 | 12/1993 | Herrman et al. | 562/35 |
| 5,324,861 | 6/1994 | Ishizaki et al. | 568/454 |
| 5,347,045 | 9/1994 | Herrmann et al. | 562/35 |
| 5,510,503 | 4/1996 | Laue et al. | 556/21 |
| 5,563,295 | 10/1996 | Takaya et al. | 562/606 |
| 5,565,398 | 10/1996 | Hermann et al. | 502/166 |
| 5,631,345 | 5/1997 | Takaya et al. | 528/392 |
| 5,631,393 | 5/1997 | Kohlpainter et al. | 556/17 |
| 5,736,480 | 4/1998 | Davis et al. | 502/155 |
| 5,801,261 | 9/1998 | Laue et al. | 556/16 |
| 5,827,794 | 10/1998 | Davis et al. | 502/166 |

FOREIGN PATENT DOCUMENTS

| | | |
|---|---|---|
| 0 133 127 | 7/1983 | (EP) . |
| 0 174 057 | 3/1986 | (EP) . |
| 0 307 168 | 3/1989 | (EP) . |
| 0 408 340 | 1/1991 | (EP) . |
| 0444 930 | 9/1991 | (EP) . |
| 0470 756 | 2/1992 | (EP) . |
| 0 478 147 | 4/1992 | (EP) . |
| 0 479 541 | 4/1992 | (EP) . |
| 2 489 308 | 9/1981 | (FR) . |
| 55-61937 | 5/1980 | (JP) . |

OTHER PUBLICATIONS

R. Noyori, et al., "BINAP: An Efficient Chiral Element for Asymmetric Catalysis," Acc. Chem. Res. 1990, 23, 345–350.

R. Noyori, "Centenary Lecture: Chemical Multiplication of Chirality: Science and Applications," Chem. Soc. Rev. 1989, 18, 187–208.

A. Miyashita, et al., "Synthesis of 2,2'–Bis9diphenylphosphino)–1,1'–binaphthyl (BINAP), an Atropisomeric Chiral Bis (triaryl) phosphine, and Its Use in the Rhodium (I) –Catalyzed Asymmetric Hydrogenation of α–(Acylamino)acrylic Acids," J. Am. Chem. Soc. 1980, 102, 7932–7934.

A. Miyashita et al., "2,2'–Bis(diphenylphosphino) –1,1'–binaphthyl (BINAP) : A New Atropisomeric Bis (triaryl) Phosphine, Synthesis and Its Use in the Rh (I) –Catalyzed Asymmetric Hydrogenation of α–(Acylamino) acrylic Acids," Tetrahedron vol. 40, No. 8, pp. 1245–1253 (1984).

T. Ohta, et al., "BINAP–Ruthenium (II) Dicarboxylate Complexes: New, Highly Efficient Catalysts for Asymmetric Hydrogenations," Inorg. Chem. 1988, 27, 566–569.

R. Noyori, et al., "Enantioselective Catalysis with Metal Complexes. An Overview," R. Scheffold (Ed.) Modern Synthetic Methods 1989, vol. 5, pp. 115–198.

Kam–to Wan & Mark E. Davis, "Ruthenium (II) –Sulfonated BINAP: A Novel Water–Soluble Asymmetric Hydrogenation Catalyst", Tetrahedron: Asymmetry vol. 4 No. 12, 1993, pp. 2461–2467.

Kam–to Wan & Mark E. Davis, "Asymmetric Hydrogenation in Water by a Rhodium Complex of Sulfonated 2,2–Bis (diphenylphosphine) –1,1'–Binaphthyl (binap)", J. Chem. Soc. Chem. Commun., 1993, pp. 1262–1264.

* cited by examiner

Primary Examiner—Paul J. Killos
(74) Attorney, Agent, or Firm—Limbach & Limbach LLP

(57) ABSTRACT

Supported phase catalysts in which the support phase is highly polar, most preferably ethylene glycol or glycerol, are disclosed. An organometallic compound, preferably a metal complex of chiral sulfonated 2,2'-bis(diphenylphosphino)-1,1'-binaphthyl is dissolved in the support phase. Such supported phase catalysts are useful for asymmetric synthesis of optically active compounds, including the asymmetric hydrogenation of prochiral unsaturated carbon-hetero atom bonds, such as ketones, imines and beta-keto esters.

10 Claims, 1 Drawing Sheet

SUPPORTED PHASE CATALYST

REFERENCE TO RELATED APPLICATIONS

This is a divisional of application Ser. No. 08/838,730, filed Apr. 10, 1997 now U.S. Pat. No. 5,935,892 which is a continuation-in-part of pending U.S. application Ser. No. 08/371,880 filed Jan. 12, 1995 now U.S. Pat. No. 5,736,480, which is a continuation-in-part of pending U.S. application Ser. No. 08/199,086 filed Feb. 22, 1994, now abandoned which applications are incorporated herein by reference.

The U.S. Government has certain rights in this invention pursuant to Grant No. CTS-9021017 awarded by the National Science Foundation.

TECHNICAL FIELD

The present invention is directed to supported phase catalyst systems in which an organometallic catalyst is solubilized in the supported phase, and the use of such catalysts in asymmetric hydrogenation reactions.

BACKGROUND OF THE INVENTION

The development of effective asymmetric reactions that enable the enantioselective formation of one chiral center over another continues to be an important area of research. One such asymmetric reaction involves the introduction of a chiral center into a molecule through the enantioselective hydrogenation of a prochiral unsaturated bond by using a transition metal catalyst bearing chiral organic ligands. Numerous chiral phosphine catalysts have been developed to enantioselectively introduce chiral centers to prochiral olefins, carbonyls and imines with high enantiomeric excess. One such class of chiral catalysts employs the chiral phosphine ligand 2,2'-bis(diphenylphosphino)-1,1'-binaphthyl (hereinafter referred to as "BINAP").

A second important area of research relates to the development of water-soluble organometallic catalysts. Conventionally, catalytically active organometallic complexes have been applied as homogeneous catalysts in solution in the organic reaction phase. Difficulties associated with recovery of the homogeneous catalysts from the reactants and products diminish the utility of these homogeneous catalysts, especially when the cost of the catalyst is high or where there is the need to isolate the reaction products in high purity.

One mode in which water soluble organometallic catalysts have been used is in two phase systems comprising an aqueous phase and a water immiscible phase (e.g. ethyl acetate-water). Separation of the organometallic catalyst from organic reactants and products is greatly simplified due to the insolubility of the catalyst in the water immiscible phase. However, in some instances, the utility of the two phase system has been limited by a lack of substrate and/or reactant solubility in the aqueous phase, by the limited interfacial area between the two phases, and by poor selectivity.

Supported phase (SP) organometallic catalysts have been developed to overcome some of the shortcomings associated with two phase reaction systems. In a supported phase system the interfacial area between the support phase, which contains the organometallic catalyst, and the water immiscible (bulk organic) phase, is greatly enhanced.

The advantages of supported phase organometallic catalyst systems have prompted further investigation into catalyst systems which will retain the beneficial characteristics thereof while further increasing yield and enantioselectivity.

SUMMARY OF THE INVENTION

Such further advantages are achieved by the present invention, which relates to supported phase catalysts in which the support phase contains a highly polar and non-aqueous liquid, such as an alcohol with two or more hydroxy groups, preferably glycerol, a triol.

In this regard, the present invention is a supported phase catalyst system wherein glycerol forms the supported phase. An organometallic compound, preferably a metal complex of chiral sulfonated 2,2'-bis(diphenylphosphino)-1,1'-binaphthyl is dissolved in glycerol. While the use of a diol, such as ethylene glycol is within the scope of the invention, the use of glycerol in the solvent support phase in a supported phase catalyst system offers the further advantage of safety due to the relatively low toxicity of glycerol as compared to ethylene glycol.

The invention further includes the use of such supported phase catalysts for asymmetric synthesis of optically active compounds containing chiral carbon-carbon and carbon-hetero atom bonds, such as the preparation of dehydronaproxen, or the asymmetric hydrogenation of ketones, imines, or beta-keto esters, such as ethyl butyrylacetate. Generally, such asymmetric reactions include those reactions in which organometallic catalysts are commonly used, such as reduction and isomerization reactions on unsaturated substrates and carbon-carbon bond forming reactions, and specifically hydrogenation, hydroboration, hydrosilylation, hydride reduction, hydroformylation, alkylation, allylic alkylation, arylation, alkenylation, epoxidation, hydrocyanation, disilylation, cyclization and isomerization reactions.

BRIEF DESCRIPTION OF THE DRAWINGS

The invention will be better understood by reference to the appended FIGS. 1A–1C which are diagrams of the preferred catalyst system of the invention.

DETAILED DESCRIPTION OF THE PREFERRED EMBODIMENT

Figure 1:
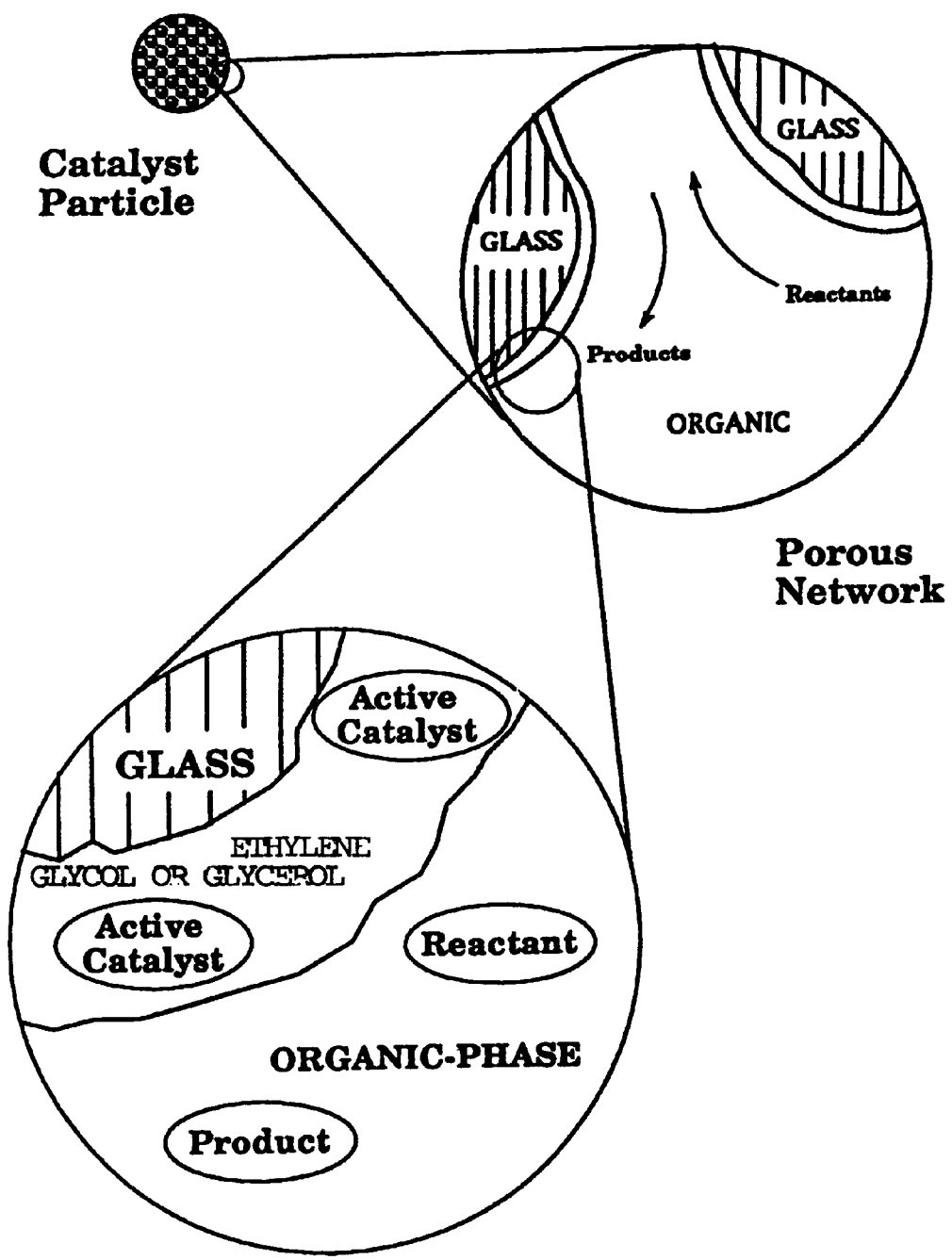

The present invention relates to an improved supported phase catalyst system, and its use in asymmetric synthesis of optically active compounds containing carbon-carbon or carbon-hetero atom bonds.

One advantage of supported phase (SP) catalysts is the simplicity of catalyst recovery. When a SP catalyst is used in an organic solvent, the organometallic catalyst is retained within the supported solution immobilized on the surface of a solid support (catalyst particle) and thus can be easily recovered by simple filtration.

With respect to the catalysts useful in the present invention, chiral sulfonated 2,2'-bis(diphenylphosphino)-1,1'-binaphthyl (BINAP-SO$_3$Na) ligands in the form of organometallic catalysts are preferred.

It is most preferred that the chiral sulfonated BINAP be tetrasulfonated (BINAP-4SO$_3$Na). Metals used to form such catalysts include, but are not limited to, rhodium, ruthenium, iridium, vanadium, lead, platinum, tin, nickel or palladium. With regard to hydrogenation reactions, ruthenium is the most preferred metal. It is also preferred that the catalyst comprise counterions, most preferably Na$^+$, K$^+$, Cs$^+$ and Ca$^{2+}$. The preferred sulfonated BINAP catalyst, [Ru(benzene)(Cl)(BINAP-4SO$_3$Na)]Cl, is structured as follows:

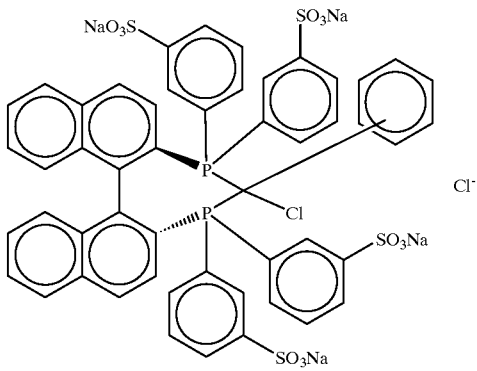

Asymmetric reactions for which the SP catalysts of the invention can be used include those reactions in which organometallic catalysts are commonly used. Such reactions include reduction and isomerization reactions on unsaturated substrates and carbon-carbon bond forming reactions, such as hydrogenation, hydroboration, hydrosilylation, hydride reduction, hydroformylation, alkylation, allylic alkylation, arylation, alkenylation, epoxidation, hydrocyanation, disylylation, cyclization and isomerization reactions. In these reactions, a catalyst is generally used to catalyze the enantioselective transformation of a prochiral unsaturated substrate. Types of prochiral unsaturated substrates asymmetrically reacted using the sulfonated BINAP catalysts include alkenes, aldehydes, ketones, thioketones, oximes, imines, enamines, allylic alcohols, allylamines, unsaturated carboxylic acids and others.

The sulfonated catalysts useful in the present invention are soluble in highly polar solvents such as alcohols with two or more hydroxy groups, for example, ethylene glycol or glycerol. The sulfonated catalysts are not soluble in nonpolar solvents such as hexane. As a result, the catalysts of the present invention may be employed in such alcohols where the alcohol is contained in or as the immobilized solvent on the surface of a solvent/catalyst support particle.

In each case, the sulfonated catalysts used in the invention are solvated by the supported phase and thus are available to catalyze the desired asymmetric reactions.

EXPERIMENTAL

Ruthenium based sulfonated BINAP catalysts are preferred because they exhibit higher stability, superior enantioselectivity, and catalyze a wider range of reactions than, for example, corresponding rhodium based sulfonated BINAP catalysts.

The following examples set forth the synthesis of chiral sulfonated BINAP catalysts and their use in a SP catalytic system. It is understood that reactions relating to either the (R)- or (S)-BINAP catalyst can be equally employed using the other enantiomer. Therefore, specific recitation to (R)- or (S)-BINAP, or derivatives thereof, are not intended to be limiting.

As used herein, an enantioselective reaction is one where one enantiotopic face is selectively attacked over the other thereby causing the formation of one enantiomer over another. Enantiomeric excess (e.e.) is a measurement of a reaction's enantioselectivity and is defined by the quantity $$\frac{(R-S)}{(R+S)} \times 100\%$$

where R and S are relative quantities of R and S enantiomers.

EXAMPLES

1. Sulfonation Of (R)-BINAP

Sulfonation of (R)-BINAP was carried out under conditions designed to minimize the formation of phosphine oxides and to selectively produce the tetra-sulfonated BINAP derivative. First, 1 g of (R)-BINAP was dissolved in 3.5 ml of concentrated sulfuric acid at 10° C. under argon. Afterward, 15 ml of fuming sulfuric acid (40 wt % sulfur trioxide in concentrated sulfuric acid) was added dropwise over 2–3 hours. The resulting solution was then stirred at 10° C. under an argon atmosphere for 3 days. In the event that the reaction mixture solidifies, it is preferred that a stepwise addition of sulfur trioxide be used rather than a dropwise addition in order to prevent solidification.

After stirring, the reaction was quenched by pouring the sulfuric acid solution into 100 ml of ice cooled water followed by the dropwise addition of 50 wt % NaOH until the solution was neutralized to pH 7. The resulting aqueous solution was then reduced to 30 ml under vacuum. 100 ml of methanol was then added to the concentrated solution in order to precipitate any sodium sulfate present in solution. The sodium sulfate was removed by filtration and the supernatant reduced under vacuum to yield a solid. The solid was then dissolved in neat methanol to remove trace amounts of sodium sulfate to yield sulfonated (R)-BINAP in a 70–75% yield.

Our earlier U.S. application Ser. No. 08/371,880 describes the characterization of the resultant sulfonated (R)-BINAP derivatives. Tetrasulfonated BINAP, which was monosulfonated on each phenyl ring, was formed at 85%. Minor products of the reaction include higher sulfonated BINAP derivatives, such as penta- and hexa-sulfonated BINAP derivatives, which are also effective as enantioselective catalysts.

2. Preparation Of Ruthenium BINAP-4 SO$_3$Na Catalyst

Ruthenium BINAP-4 SO$_3$Na catalyst was prepared by reacting [Ru(benzene)Cl$_2$]$_2$ with two equivalents of (R)-BINAP-4SO$_3$Na in a 1:8 benzene/methanol solvent to yield [Ru(benzene)Cl[(R)-BINAP-4 SO$_3$Na]]Cl. $^{31}$P NMR (CD$_3$OD): d.d. δ=63.0, δ 68.8 ppm J=45 Hz. Specifically, 0.0010 g of [Ru(benzene)Cl$_2$]$_2$ was stirred with 0.0050 g BINAP-SO$_3$Na in 4.5 ml of a 1:8 benzene/methanol solvent at 55° C. under argon for 1–2 hours. The resulting solution was then vacuum dried at room temperature ("dried" catalyst).

3. Asymmetric Hydrogenation Using Ethylene Glycol As The Supported Phase

The organometallic ruthenium catalyst of Example 2 exhibits a solvent dependent enantioselectivity when operated homogeneously. Although this homogeneous organometallic ruthenium catalyst is effective in promoting the asymmetric hydrogenation of 2-(6'-methoxy-2'-naphthyl) acrylic acid (substrate 1) with 96% e.e. in neat methanol, the enantioselectivity drops to about 80% e.e. in water. As a result, the enantioselectivity of the catalyst when supported in an aqueous phase, i.e., a hydrated supported aqueous phase (SAP) catalyst, is bounded by the intrinsic enantioselectivity limit of the organometallic ruthenium complex in neat water. Hence, further refinements on the SAP catalyst are made, enabling the development of a practical, general-use, heterogeneous, chiral catalyst.

In this example, we describe the detailed design and synthesis of another new heterogeneous catalyst and its use in the asymmetric hydrogenation of 2-(6'-methoxy-2'-naphthyl)acrylic acid to naproxen. We further describe the composition of this new catalyst, a new method for the activation of the "dried" catalyst, and reaction conditions that prevent leaching.

The catalyst system of this example is shown in FIGS. 1A–1C. FIGS. 1A–1C show the use of ethylene glycol and/or glycerol as the support phase for an organometallic catalyst such as sulfonated BINAP.

The materials used in this example are as follows: controlled pore glass CPG-240 (a narrow pore-size distribution glass: mean pore diameter=242 Å, pore volume=0.89 ml/g, surface area=79 m$^2$/g, mesh size=120/200), benzeneruthenium (II) chloride dimer, ethyl acetate, cyclohexane, chloroform, ethylene glycol and triethylamine in their highest purity available. Unless otherwise noted, the sodium salt of tetra-sulfonated BINAP is prepared as above (Example 1) and all manipulations are performed under argon or nitrogen. Deionized water, distilled over potassium permanganate are used in all operations requiring water. All solvents, including water, are degassed by four to five freeze-pump-thaw cycles.

The catalyst is prepared and activated in the following manner. The active organometallic ruthenium catalyst, [Ru(BINAP-4SO$_3$Na)(benzene)Cl]Cl, is prepared and impregnated onto the CPG support. The water content of this "dried" catalyst is estimated by thermogravimetric analysis to be 1.9 wt %, while the ruthenium contents were 1.2–2.5×10$^{-5}$ mol/g and anhydrous ethylene glycol is used to activate the "dried" catalyst. The activation of the catalyst is performed by two different techniques: (A) by the in-situ activation with ethylene glycol in ethyl acetate (ethylene glycol partitions between the organic solvent and the surface of the CPG), and (B) as follows. The "dried" catalyst is stirred in ethyl acetate that had been previously premixed with a controlled amount of ethylene glycol. The highly polar ethylene glycol must be allowed to partition between the ethyl acetate phase and the CPG surface for about one hour. Because of a small partition coefficient for ethylene glycol between the CPG support and the ethyl acetate, most of the ethylene glycol should remain in the bulk organic phase upon contact with the "dried" catalyst. This procedure is then repeated. The bulk organic phase is removed by filtration and the resulting catalyst is washed several times with a 1:1 chloroform and cyclohexane mixture that had been pre-mixed with ethylene glycol.

Asymmetric hydrogenations of 2-(6'-methoxy-2'-naphthyl) acrylic acid are conducted at various temperatures in a 25 ml stainless steel Parr batch reactor. Special care should be taken to avoid introducing oxygen into the reaction mixture at all times. Both the neat ethyl acetate and the 1:1 mixture of chloroform/cyclohexane may be used as the bulk organic phase (5 ml). The hydrogenation reaction is best measured by $^1$H NMR spectroscopy and the enantiomeric excess (e.e.) determined by HPLC.

The asymmetric hydrogenation of 2-(6'-methoxy-2'-naphthyl)acrylic acid (substrate 1) is chosen to be our model reaction. Our work shows that the presence of water tends to lower the enantioselectivity in the homogeneous hydrogenation of the substrate in methanolic solvents. Aquation of the ruthenium-chloro bond in water is, therefore responsible for this solvent dependent enantioselectivity. To prevent the cleavage of the ruthenium-chloro bond, anhydrous ethylene glycol is used here in place of water. A $^{31}$P NMR spectrum of the ruthenium complex in 1:1 CD$_3$OD/ethylene glycol reveals the same two doublets (δ=63.0 and 68.8 ppm; J≈45 Hz) as are found in neat methanol indicating that the ruthenium-chloro bond in [Ru(BINAP-4SO$_3$Na)(benzene)Cl]Cl is still intact. Upon addition of water, only a singlet (δ=57.5 ppm) is observed in the $^{31}$P NMR spectrum. These data suggest that a rapid hydrolysis of the ruthenium-chloro bond has occurred in the presence of water. As a result, hydrogenations of substrate 1 are carried out in the presence of ethylene glycol. Similar enantioselectivities (88–89%) are observed for reactions carried out in neat methanol, 1:1 methanol/ethylene glycol and also in neat ethylene glycol. These findings further support the premise that the cleavage of the ruthenium-chloro bond has a detrimental effect on enantioselectivity. An e.e. of only 79% is observed in a 1:1 MeOH/H$_2$O solvent mixture. Thus, since the highly polar ethylene glycol is not miscible with most organic solvents, it can be used as a substitute for the aqueous phase in the SAP system; it replaces the role of water in the immobilization of the ruthenium catalyst onto the CPG support.

This new heterogeneous catalyst now comprises or consists of a ruthenium organometallic complex dissolved in a film of ethylene glycol which is supported on a high-surface-area hydrophilic (e.g. CPG) support (FIGS. 1A–1C).

With the in-situ activation using ethylene glycol, enantioselectivities are found to increase with increasing amount of ethylene glycol in the system. The enantioselectivities as a function of ethylene glycol content are listed in Table 1 (reaction conditions: substrate/ruthenium=30, [substrate]=3.6×10$^{-3}$ M, solvent volume=5 ml, pressure=1400 psig, T=24° C., stirring speed=350 rpm). At a maximum ethylene glycol loading of 400 μl in 5 ml of ethyl acetate an 87.7% e.e. is observed, while only 45.0% e.e. is found for the system with 75 μl of ethylene glycol. These results are in agreement with our previous findings for the hydrated SAP systems where the higher the water content the higher the enantioselectivity. More importantly, the new heterogeneous catalyst with ethylene glycol as a substitute for the aqueous phase achieves the same high enantioselectivity as its homogeneous analogue in neat methanol. By lowering the reaction temperature to 3° C., the e.e. is increased to 94.8%. However, unlike the homogeneous analogue in neat methanol, addition of triethylamine to the heterogeneous catalyst is found to have a detrimental effect on enantioselectivity. An almost 15% drop in e.e. is observed at room temperature upon addition of triethylamine. This is rather unexpected since we believe that the active ruthenium catalyst is nearly the same as the one in neat methanol. Solvation of the ruthenium complex with ethylene glycol may be responsible for the decline in enantioselectivity upon addition of base, but the detailed mechanism is still unclear. A similar drop in e.e. is also reported in our original hydrated SAP system.

For long-term stability, the heterogeneous catalyst must also remain assembled. To test for this type of stability, the following self-assembly test is performed: 1.1×10$^{-6}$ moles of [Ru(BINAP-4SO$_3$Na)(benzene)Cl]Cl is dissolved in 400 μl of ethylene glycol and loaded into a 25 ml Parr reactor. 5.7×10$^{-5}$ moles of substrate 1 in 5 ml of ethyl acetate is then added. Finally, 0.1 g CPG-240 is added. The reactor is pressurized to 1,400 psig with hydrogen and stirred at 350 rpm and at room temperature. The reaction is stopped after one hour and analyzed. A control experiment is carried out in using exactly the same procedure with the exception that no CPG is added. Complete conversion of substrate 1 is observed when CPG is added, while no detectable conversion is found in the control experiment. After the reaction, the CPG support turns pale yellow and the bulk organic phase is colorless. These results indicate that, under the reaction conditions, the individual components of the heterogeneous catalyst self-assemble into a more thermodynamically stable supported-catalyst configuration. Therefore, the reverse, i.e., the separation of the solution and complex from the support, is unlikely to occur under reaction conditions because such a separation is not thermodynamically favored. These results also support the inference that the reaction chemistry is taking place at the liquid-liquid interface. In the control experiment, most of the added ethylene glycol dissolved into the bulk organic phase and left behind small droplets of catalyst solution. The limited interfacial area of the catalyst solution that remains immiscible with the bulk organic phase results in the lack of activity in the control experiment.

Unlike a hydrated SAP catalyst, traces of ruthenium are found in the reaction filtrates. The extent of ruthenium leaching was found to be correlated with the ethylene glycol content in the organic phase as evidenced by the data shown in Table 2. Since ethylene glycol is less polar than water, it is at least 3 times more soluble than water in ethyl acetate. The higher solubility of ethylene glycol in ethyl acetate is likely responsible for the observed leaching of ruthenium into the bulk organic phase. In order to minimize the leaching of ruthenium into the bulk organic phase, a new method of activation of the "dried" catalyst with ethylene glycol was devised, and is described below.

The "dried" catalyst is activated by stirring it in an ethylene glycol/ethyl acetate solvent mixture. After equilibration for an hour at room temperature, the solid catalyst is filtered and dried at low vacuum (0.2 atm.). The procedure is then repeated. Only a thin film of non-volatile ethylene glycol is deposited onto the solid catalyst. The amount of ethylene glycol in the film is approximately the same as that found with the original in-situ activation procedure, and a similar degree of mobility of the ruthenium complex on the support is to be expected. However, in this embodiment an ethylene glyco-saturated organic phase is used so as to maintain the integrity of this film during the reaction. To minimize the amount of ethylene glycol used in the bulk organic phase, a 1:1 solvent mixture of cyclohexane and chloroform (for solubilization of substrate) is used. As shown in Table 3, the same high enantioselectivity (88.4% e.e. at room temperature) is still obtained with this kind of activation procedure and more importantly, no ruthenium is found in the reaction filtrate at a detection limit of 32 ppb. By lowering the reaction temperature to 3° C., an 95.7% e.e. is obtained with this new heterogeneous catalyst. As shown in Table 3, the present system is already as enantioselective as its homogeneous analogue (95.7% vs. 96.1%). Thus, recycling of the catalyst is possible without any loss in enantioselectivity.

Using the new formulation, another self-assembly test is again carried out to verify the long-term stability of the catalyst. $1 \times 10^{-7}$ moles of the ruthenium complex in 50 $\mu$l of ethylene glycol is mixed with $4 \times 10^{-6}$ moles of substrate in 5 ml of 1:1 chloroform/cyclohexane. 0.2 g of CPG-240 are added, and then the reactor is pressurized to 1,400 psig with hydrogen and the mixture is stirred at room temperature for 2 hours. Complete conversion is observed. However, less than 2% conversion is found from the control experiment where no CPG was added. These results again indicate that, under these new reaction conditions, the individual components of the present catalytic system self-assemble into the more stable supported-catalyst configuration.

With comparable activity and enantioselectivity to the homogeneous catalyst, the present heterogeneous catalyst can be considered a genuine hybrid of homogeneous and heterogeneous catalysts. As compared to the asymmetric hydrogenation catalysts anchored in modified USY zeolites, Corma et al., *J.C.S., Chem. Commun.* 1253 (1991); Sanchez et al., *J. Mol. Catal.* 70, 369 (1991), this example of our invention has several distinguishing features. The CPG support possesses large and uniform pore diameters that allow large bio-substrate access to the catalytic sites. Also, CPG supports are commercially available in a wide range of pore diameters (75–3000 Å); for the zeolite-supported catalyst, the small pore size (~8 Å) limits the size of substrate. Furthermore, the active rhodium complex is covalently bonded to the zeolite framework and reasonable activity can only be reached at elevated temperature (60° C.). In contrast, the active ruthenium complex in the present system is dissolved in ethylene glycol, which is immobilized as a thin film on the CPG support. At molecular level, this method of immobilization yields a heterogeneous catalyst that is basically the same as its homogeneous analogue, thus allowing for the high enantioselectivity and activity.

TABLE 1

Enantioselectivities in the reduction of substrate as a function of ethylene glycol content in organic phase[†]

| Ethylene Glycol content ($\mu$l) | e.e. (%) |
|---|---|
| 75 | 45.0 |
| 150 | 72.1 |
| 270 | 82.1 |
| 350 | 84.2 |
| 350 | 71.3[a] |
| 350 | 91.1[b] |
| 400 | 87.7 |
| 400 | 94.8[b] |

[†]catalysts were activated by in-situ organic-phase impregnation with 5 ml of ethyl acetate; substrate/ruthenium = 30; pressure = 1400 psig and at room temperature
[a]with addition of triethylamine
[b]reaction temperature = 3° C.

TABLE 2

Ruthenium leaching as a function of ethylene glycol content in the reduction of substrate*

| Ethylene Glycol content[†] ($\mu$l) | Ruthenium[‡] (ppm) |
|---|---|
| 150 | 0.17 |
| 270 | 0.27 |
| 350 | 0.23[a] |
| 400 | 0.37 |

*substrate/ruthenium = 30; $H_2$ pressure = 1350–1450 psig; reaction temp. = 24° C.; stirring speed = 350 rpm
[†]in-situ catalyst activation with method (A)
[‡]ruthenium content in the reaction filtrates
[a]reaction temperature = 3° C.

TABLE 3

Enantioselectivities in the reduction of substrate with ruthenium catalysts in different configurations*

| Catalyst | Solvent | e.e. (%) |
|---|---|---|
| Heterogeneous[‡] | 1:1 $CHCl_3$/Cyclohexane | 88.4 |
| Heterogeneous[‡] | 1:1 $CHCl_3$/Cyclohexane | 95.7[a] |
| Heterogeneous[†] | AcOEt | 87.7 |
| Heterogeneous[†] | AcOEt | 94.8[a] |

TABLE 3-continued

Enantioselectivities in the reduction of
substrate with ruthenium catalysts in
different configurations*

| Catalyst | Solvent | e.e. (%) |
|---|---|---|
| Homogeneous# | MeOH | 88.2 |
| Homogeneous# | MeOH | 96.1[b] |

*substrate/ruthenium = 30–100; H$_2$ pressure = 1350–1450 psig; reaction temp. = 24° C.; stirring speed = 350 rpm
‡catalyst activation with method (B)
†in-situ catalysts activation with method (A)
Wan et al., J. Catal. 148, 1 (1994)
[a]reaction temperature = 3° C.
[b]reaction temperature = 3° C. in Wan et al., J. Catal. 148, 1 (1994)

4. Asymmetric Hydrogenation Using Glycerol As The Supported Phase

In the above example, we described an asymmetric reaction on a substrate containing a prochiral unsaturated carbon-carbon bond. Asymmetric reactions on subtrates containing prochiral unsaturated carbon-hetero atom bonds can also be performed using the supported phase system of Example 3, for example, the hydrogenation of ketones, imines and beta-keto esters. These same reactions can be performed as effectively with glycerol substitued for ethylene glycol as the support phase, with the added benefit of glycerol being a much safer and easier to use solvent than ethylene glycol.

In this example, we describe the asymmetric hydrogenation of ethyl butyrylacetate to the corresponding chiral beta-hydroxy carboxylic ester using a supported phase catalyst system wherein the supported phase is glycerol. The catalyst system of this example, as shown in the Figure, includes a ruthenium organometallic complex dissolved in a film or layer of glycerol which is supported on a high-surface-area hydrophilic solid particle, e.g. controlled pore glass (CPG). The Figure shows the use of glycerol as the support phase for an organometallic catalyst such as sulfonated BINAP. (The glycerol is "supported" by the CPG, and "supports" the organometallic catalyst dissolved therein.)

The materials used in this example were as follows: controlled pore glass CPG-240 (a narrow pore-size distribution glass: mean pore diameter=242 Å, pore volume=0.89 ml/g, surface area=79 m$^2$/g, mesh size=120/200), benzeneruthenium (II) chloride dimer, ethyl acetate, cyclohexane, chloroform, glycerol and triethylamine in their highest purity available. The sodium salt of tetra-sulfonated BINAP was prepared as above (Example 1) and all manipulations were performed under argon or nitrogen. Deionized water, distilled over potassium permanganate was used in all operations requiring water. All solvents, including water, were degassed by four to five freeze-pump-thaw cycles.

The catalyst was prepared and activated in the following manner. The active organometallic ruthenium catalyst, [Ru (BINAP-4SO$_3$Na)(benzene)Cl]Cl, was prepared as above (Example 3) and impregnated onto the CPG support. The water content of this "dried" catalyst was estimated by thermogravimetric analysis to be 1.9 wt %, while the ruthenium contents were 0.5–1.0×10$^{-4}$ mol/g. Anhydrous glycerol was used to activate the "dried" catalyst in-situ (glycerol partitions between the bulk phase organic solvent and the surface of the CPG) as follows: 200 mg of the "dried" catalyst in 50–60 μl of anhydrous glycerol was added to 210 mg of ethyl butyrylacetate dissolved in 5 ml of bulk organic phase. The bulk organic phase consisted of a 9:1 mixture of cyclohexane/ethyl acetate saturated with glycerol.

Asymmetric hydrogenations of ethyl butyrlacetate were conducted at 85° C. in a 25 ml stainless steel Parr batch reactor. Special care was taken to avoid introducing oxygen into the reaction mixture at all times. The hydrogenation reaction was measured by $^1$H NMR spectroscopy and the enantiomeric excess (e.e.) determined by HPLC. Complete conversions were found after stirring at 85° C. for 24 hours. Beta-hydroxy carboxylic esters were formed at 93.4% e.e. (S).

These results compared favorably with the use of ethylene glycol as the support phase. The same reaction conditions, with ethylene glycol substituted for glycerol, yielded complete conversions at 24 hours with beta-hydroxy carboxylic esters formed at 95.0% e.e. (S). Thus, glycerol is as effective as a support phase, with the added advantage that glycerol is much safer to use as a support phase due its lower toxicity.

Thus, alcohol containing solvents, i.e. alcohols having two or more hydroxy groups (diols and triols), have been shown to be useful as the supported phase for solubilizing the organometallic catalysts of the invention.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. For example, those skilled in the art will appreciate that the supported phase of the invention can be another solvent in which the organometallic catalyst can be dissolved but which will not substantially dissolve in the bulk organic phase.

What is claimed is:

1. A method for conducting an asymmetric reaction to a prochiral unsaturated bond contained within a compound comprising the step of contacting said compound with a supported liquid phase catalyst comprising an organometallic compound which comprises a metal and a chiral sulfonated 2,2'-bis(diphenylphosphino)-1,1'-binaphthyl solubilized in a solvent having at least two alcohol groups,
   wherein each phenyl group of the 2,2'-bis (diphenylphosphino)-1,1'-binaphthyl is at least monosulfonated, and
   wherein the degree to which the 2,2'-bis (diphenylphosphino)-1,1'-binaphthyl is sulfonated is selected from the group consisting of tetrasulfonated, pentasulfonated, and hexasulfonated.

2. A method according to claim 1 wherein the asymmetric reaction is selected from the group consisting of hydrogenation, hydroboration, hydrosilylation, hydride reduction, hydroformylation, alkylation, allylic alkylation, arylation, alkenylation, epoxidation, hydrocyanation, cyclization and disilylation.

3. A method according to claim 2 wherein the asymmetric reaction is hydrogenation.

4. A method according to claim 1 wherein said solvent is ethylene glycol.

5. A method according to claim 1 wherein said solvent is glycerol.

6. A method according to claim 3 wherein said prochiral unsaturated bond is a prochiral unsaturated carbon-hetero atom bond.

7. A method according to claim 6 wherein said prochiral unsaturated carbon-hetero atom bond comprises a prochiral ketone group.

8. A method according to claim 6 wherein said prochiral unsaturated carbon-hetero atom bond comprises a prochiral imine group.

9. A method according to claim 6, wherein said compound is a prochiral beta-keto ester.

10. A method according to claim 9, wherein said beta-keto ester is ethyl butyrylacetate.

* * * * *